United States Patent [19]
Jin et al.

[11] Patent Number: 5,952,548
[45] Date of Patent: Sep. 14, 1999

[54] SOYBEAN GLUCANASES, COMPOUNDS WHICH ENCODE THEREFOR AND RELATED METHODS

[75] Inventors: Wei Jin; Harry T. Horner; Reid G. Palmer, all of Ames; Randy C. Shoemaker, Story City, all of Iowa

[73] Assignee: Iowa State University Research Foundation, Inc., Ames, Iowa

[21] Appl. No.: 08/963,743

[22] Filed: Nov. 4, 1997

[51] Int. Cl.$^6$ .......................... C12N 15/29; C12N 15/56; C12N 15/82; A01H 5/00; A01H 5/10

[52] U.S. Cl. .......................... 800/303; 800/274; 800/278; 800/284; 800/298; 800/312; 435/69.1; 435/200; 435/209; 435/320.1; 435/468; 536/23.6

[58] Field of Search .......................... 536/23.6; 435/69.1, 435/172.3, 200, 209, 320.1, 468; 800/205, 250, 255, DIG. 26, 274, 278, 284, 298, 303, 312

[56] References Cited

U.S. PATENT DOCUMENTS 5,477,001 12/1995 Sass et al. ............................... 800/205
5,554,743 9/1996 Bennett et al. .......................... 536/23.6

OTHER PUBLICATIONS

Napoli et al. Plant Cell 2: 279–289, Apr. 1990.
Smith et al. Nature 334: 724–726, Aug. 1988.
Tsuchiya et al. Plant Cell Physiol. 36(3): 487–494, 1995.
Takeuchi et al. Plant Physiol. 93: 673–682, 1990.
Christon et al. Proc. Natl. Acad. Sci. USA 86: 7500–7504, Oct. 1989.
Vol. 83(6) *Am. J. Bot.* p. 42, abstract 121 (1996) Jin et al.

*Primary Examiner*—David T. Fox
*Attorney, Agent, or Firm*—Kristine H. Johnson; Macheledt Bales & Johnson LLP

[57] ABSTRACT

The present invention provides 12 different sequences for soybean β-1,3-glucanases and the proteins for which they encode. Also provided are methods for the utilization of knockout mutants of the sequences which are useful for engineering genic male-sterile plants. Other methods and materials related to these sequences are also provided.

13 Claims, No Drawings

SOYBEAN GLUCANASES, COMPOUNDS WHICH ENCODE THEREFOR AND RELATED METHODS

BACKGROUND OF THE INVENTION

The present inventors recently characterized a genic male-sterile mutant of soybean: 83(6) *Am. J. Bot.* 42, abstract 121(1996); Jin et al., 10 *Sex Plant Reprod.* 13 (1997). Microscopic analysis of the mutant showed the callose encasement of the microspores was retained at an inappropriate developmental stage. The persistent callose encasement resulted in no release, and subsequent degeneration of the microspores. Other results in these publications showed that callase, the enzyme which is responsible for digestion of the callose wall, was inactive. The reason for the inactivity was not elucidated at that time.

Other publications by the present inventors identified the callase as a β-1,3-glucanase. Abstract P14, *Genetics Society of Canada* (June 1997); 114(3) *Plant Physiology* 172, abstract 842 (June 1997); 84(6) *Am. J. Bot.* 63, abstract 182 (June 1997).

Soybean β-1,3-glucanases have been cloned in the past. For example, U.S. Pat. No. 5,477,001 disclosed cloned β-1,3- glucanases from soybean. The gene products are implicated in disease resistance. No disclosure of the involvement of β-1,3- glucanases as a callase is described in the patent. Non-soybean glucanases, such as those described in U.S. Pat. No. 5,554,743 describe β-1,3-glucanases involved in cell wall polysaccharide degradation.

A search of the National Institutes of Health BLAST database disclosed a line of soybean "*Glycine max* cv. Century 84" with cloned β-1,3-glucanases. None of the sequences found were identical to the presently-claimed sequences. The following is a table of the results of the search.

| SEQ ID NO | CLOSEST HOMOLOGY | REFERENCE |
| --- | --- | --- |
| 1 | 85% (soybean glucanase) | U.S. Pat. No. 5477001, Seq 8; same as WO9413790, Seq 15 |
| 2 | 98% (soybean endoglucanase) | none available |
| 3 | 91% (Century 84) | 26 Crop Science 199 (1986) |
| 4 | 97% (soybean glucanase) | U.S. Pat. No. 5477001, Seq 8; same as WO9413790, Seq 15 |
| 5 | 76% (Century 84) | 26 Crop Science 199 (1986) |
| 6 | 91% (Century 84) | 26 Crop Science 199 (1986) |
| 7 | 54% (unknown) | U.S. Pat. No. 5614395, Seq 13; same as WO9413790, Seq 15 |
| 8 | 85% (soybean glucanase) | U.S. Pat. No. 5477001, Seq Id 8; same as WO9413790, Seq 15 |
| 9 | 75% (Century 84) | 26 Crop Science 199 (1986) |
| 10 | 97% (Century 84) | 26 Crop Science 199 (1986) |
| 11 | 76% (Century 84) | 26 Crop Science 199 (1986) |
| 12 | 96% (soybean glucanase) | U.S. Pat. No. 5477001, Seq Id 8; same as WO9413790, Seq 15 |

The U.S. Pat. No. 5,477,001 does not disclose or suggest the present invention, because the sequences described herein are not disclosed. Moreover, the emphasis in the U.S. Pat. No. 5,477,001 is the use of a particular soybean glucanase to resist plant diseases. In certain aspects of the present invention, the focus is on the elimination of active soybean glucanases; the U.S. Pat. No. 5,477,001 therefore teaches away from those aspects of the present invention.

Century 84 is a line of soybean which was released jointly by the Ohio Agricultural Research and Development Center, The Ohio State University and the USDA which contained over-expressed glucanase for the purpose of disease resistance. Registration Number 188,26 *Crop Science* 199 (1989).

Citation of the above documents is not intended as an admission that any of the foregoing is pertinent prior art. For example, in some instances above, the publication was less than one year before the filing date of this patent application. All statements as to the date or representation as to the contents of these documents is based on subjective characterization of information available to the applicant at the time of filing, and does not constitute an admission as to the accuracy of the dates or contents of these documents.

SUMMARY OF THE INVENTION

It is therefore an object of the present invention to provide sequences useful to engineer male-sterile soybean lines.

It is a further object to provide methods to engineer male-sterile soybean lines.

It is yet another object to provide male-sterile soybean seeds.

It is yet another object to provide male-sterile soybean plants.

In all of the above embodiments, it is an object to provide seed mixes with male-sterile and female-fertile seeds.

It is also an object of the invention to provide materials such as vectors for genetic engineering male-sterile soybean lines.

It is an additional object to provide a method to improve seed germination using the materials herein disclosed.

Lastly, it is therefore an object of the present invention to provide sequences useful to engineer disease-resistant soybean lines.

DEFINITIONS

For the purposes of the present application, the following terms have the following meanings. All other terms have the meaning as generally recognized in the art.

"Knockout construct" means a DNA sequence which has been altered via any known means, for example, deletion, insertion, point mutation or rearrangement, so as to eliminate the function of the naturally-occurring β-1,3 glucanase of the pod and flower bud of a soybean plant gene product, but not so as to alter the ability of the DNA sequence to recombine with the naturally-occurring sequence.

"Knockout mutants" are cells, embryos or plants in which a naturally-occurring β-1,3-glucanase gene has been replaced through genetic engineering with a knockout construct, so as to result in a male-sterile phenotype.

DETAILED DESCRIPTION OF THE INVENTION

The present invention provides twelve different sequences for soybean β-1,3 glucanases and the proteins for which they encode. The DNA sequences are as follows:

| SEQ ID NO | SEQUENCE |
|---|---|
| 1 | CGGGATCCGGGGTGTGTTACGGCATGATGGGCGACAATCTACCACCGGCAAATGAAGTTGTAAGTCTTTACAAATCCAACGACATAA TGAGAATGAGAATCTATAATCCTGATCAAGCTGCTTTACAAGCACTGGGAAATTCGGGCATTGAGCTTATTCTTGGGGTGCTCCACC AAGACCTTCAAGGCCTTGCCACCAATGCTAGCACTGCTCAACAATGGGTGCAAAGTAACGTGTTGAACTTTTGGCCTAGTGTCAAAA TCAAGCACGTGGTAGTTGGCAACGAAATCAATCCTGTGGGAAGCTCTTCTGAGTTTGCCCAATATGTTCTACCTGCAATCCAAAACA TATACCAAGCTATAAGAGCTCAAGGCCTTCAAGATCTAATCAAGGTTACAACAGCTATTGACATGACCCTGTTAGGAAACTCCTACC CCCCATCACAAAGCTACTTCAGGACTGATGTGAGATCATACTTAGACCCCATAATTGGGTACTTGGTATATGCAAATGCACCTTTAC TAGCCAATGTGTTGCCTTATTTTAGTTACTCCAATAACCCGATTGACATATCACTTTCCTATGCTCTTTTTAACTCAACAAATGTTG TGGTTTGGGATGGTCAATATGGGTACCAAAATTTGTTTGATGCTATGTTGGATGCGGTGCATGTTGCAATTGATAACACAGGGATTG GTTATGTGGAGGTTGTTGTATCCGAGAGAGGTTGGCCGAATTCCG |
| 2 | CGGGATCCGGCGTGTGTTATGGAAGACTTGGCAACAACTTACCAACCCCTCAAGAAGTTGTGGCCCTCTACAATCAAGCCAACATTC GCAGGATGCGAATCTACGGTCCAAGCCCAGAAGTCCTCGAAGCACTAAGAGGTTCCAACATTGAGCTTTTGCTAGACATTCCAAAT GACAACCTCAGAAACCTAGCATCTAGCCAAGACAATGCAAACAAATGGGTGCAAGACAACATCAAAAACTATGCCAACAATGTCAG ATTCAGATACGTTTCAGTGGGAAATGAAGTGAAACCCGAACACTCATTTGCACAATTTCTAGTGCCTGCATTGGAAAACATTCAGA GGGCCATTTCTAATGCTGGCCTTGGAAACCAAGTAAAAGTTTCCACTGCCATTGATACTGGTGCCTTGGCAGAATCATTCCCACCA TCAAAGGGTTCCTTCAAATCTGATTATAGAGGAGCATATCTTGATGGTGTCATCAGATTTCTAGTGAACAATAATGCCCCATTAAT GGTTAATGTGTACTCTTACTTCGCTTACACTGCAAACCCTAAGGACATTAGTCTTGACTATGCACTTTTTAGGTCTCCTTCGGTGG TAGTGCAAGATGGTTCACTTGGTTACCGTAACCTCTTTGATGCTTCGGTTGATGCTGTTTATGCTGCATTGGAGAAAGCAGGAGGAG GGTCATTGAACATAGTTGTGTCTGAGTGAGGATGGCCGAATTCCG |
| 3 | CGGGATCCGGAGTTTGCTATGGAGTACTCGGTAATAATCTACCATCAAGGCAAGAAGTTGTGGACTTGTATAAAACAAATGGGATAG GTAGAATGCGTATATACTATCCAGATGAAGAAGCGCTCCAAGCCCTTAGAGGTTCAGGCATTGAGTTGATTATGGACGTGGCTAAG GAAACCCTTCAATCAATGACAGACCCCAATGCTGCTACAGATTGGGTCAATAAGTATGTTACAGCCTACTCGCAAGACGTCAATTTC AAGTACATCGCTGTTGGAAATGAAATTCACCCCAATACCAATGAGGCACAGTACATTCTATCTGCCATGACCAACATTCAGAATGC AATTTCATCAGCCAATTTACAAATCAAGGTGTCAACAGCAATAGACTCTACTTTCATTGCTCCGCCCTCCTATCCACCCAATGATG CTGTTTTCACTAGCGATGCAGAGCCATATGTAAAACCCATAATAGACTTCCTAGTGAGAAATGAGGCGCCACTTCTTGCCAATGTG TACCCTTACTTTGCTTATGCGAATGATCAACAAAACAGTATTCCTCTTGCCTATGCTCTTTTTACCCAACAAGGAAACAACGACGC TGGGTACCAAAACCTCTTCGATGCTATGTTGGATTCAATATACGCTGCAGTGGAGAAAGTGGGAGCATCCAATTTGCAGATAGTGG TTTCTGAATCTGGTTGGCCGAATTCCG |
| 4 | CGGGATCCGG GGTATGTTAT GGCATGCTGG GCAACAATCT ACCATCAGCA AACGAAGTTA TAGGTCTTTA TAGATCAAAT AACATAAGGA GAATGAGACT CTATGATCCT AATCAAGCTG CTCTAGAAGC ACTTAGAAAT TCTGGCATTG AACTCATTCT TGGGGTGCCA AACTCTGACC TTCAAGGCCT TGCCACCAAT CCTGACACTT CTCGTCAATG GGTGCAAAAA AACGTGTTGA ACTTTTGGCC TAGTGTCAAA ATCAAGTACG TGGCAGTTGG AAATGAACTG AGTCCCGTTG GACGCTCTTC TTCGGTAGCC CAATATGTTC TACCTGCCAT CCAAAATGTA TACCAAGCAA TAAGAGCTCA AGGCCTTCAT GATCAAATCA AGGTTTCAAC ATCTATTGAC ATGACCCTAA TAGGAAACTC TTTCCCTCCA CCGCAAGGTT CCTTCAGGGG TGATGTGTGA TCATACCTAG ATCCCATAAT TGGGTACTTG GTATATGCAA ATGCACCATT ACTAGTCAAT GTGTACCCTT ATTTTAGTTA CACTGGTAAC CCCCGTGACA TATCACTTCC CTATGCTCTT TTCACAGCAC CAAATGTTGT GGTATGGGAT GGTCAATATG GGTACCAAAA TTTGTTTGAT GCTATGTTGG ATTCAGTACA TGCAGCCATT GATAACACTA AGATTGGTTA TGTGGAGGTT GTTGTATCCG AAAGCGGATG GA |
| 5 | CGGGCATCCGGTGTCTGTTACGGAGGAAATGGAAACAATCTACCAACAAAGCAAGCAGTGGTGGATCTTTACAAATCAAACAGAATA |

| SEQ ID NO | SEQUENCE |
|---|---|
|  | GGCAAAATCCGTTTATACTATCCAGACGAAGGAGTCCTTCAAGCCCTCAGAGGTTCAAACATAGAGGTGATCCTCGGTGTCCCTAAT |
|  | GACCAACTTCAATCTCTCACCAACGCTGGAGCTGCCACAAATTGGGTCAACAAGTACGTGAAAGCATACTCACAAAACGTGAAATTC |
|  | AAGTACATTGCAGTTGGTAACGAAATTCACCCTGGTGACTCTTTAGCAGGGTCTGTACTTCCAGCACTTGAAACCATTCAGAAAGCA |
|  | ATTTCTGCCGCCAATTTACAAGGCCAAATGAAGGTGTCAACAGCAATAGACACCACTTTACTTGGCAACTCTTACCCACCAAAAGAT |
|  | GGCGTTTTCAGCAGTAGTGCAAGTTCATACATAAGACCAATTGTAAACTTTTTAGCAAGAAATGGAGCCCCACTTCTCGCAAACGTG |
|  | TACCCTTACTTCGCCTATGTTAACAACCAACAAAGCACTGGTCTTGACTATGCCTTGTTTACTAAACATGGTAACAACGAGGTTGGG |
|  | TACCAAAACCTGTTTGATGCAT |
|  | TGTTGGATTCTCTATACGCTGCTCTTGAGAAAGTAGGGGCACCAAATGTGAAGGTTGTTGTGTCTGAAAGAGGTTGGCCGAATTCCG |
| 6 | CGGGATCGGGGAGTATGTTACGGGAGTACTCGGTAATAATCTACCATCAAGGCAAGAAGTTGTGGACTTGTATAAAACAAATGGGA |
|  | TAGGTAGAATGCGTATATACTATCCAGATGAAGAAGCACTCCAAGCCCTTAGAGGTTCAGGCATTGAGTTGATTATGGACGTGGCT |
|  | AAGGAAACCCTTCAGTCAATGACAGACCCCAATGCTGCTACAGATTGGGTCAATAAGTATGTTACAGCCTACTCGCAAGACGTCAA |
|  | TTTCAAGTACATCGCTGTTGGAAATGAAATTCACCCCAATACCAATGAGGCACAGTACATTCTATCTGCCATGACCAACATTCAGA |
|  | ATGCAATTTCATCAGCCAATTTACAAATCAAGGTGTCAACAGCAATAGACTCTACTTTCATTGCTCCGCCCTCCTATCCACCCAAT |
|  | GATGCTGTTTTCACTAGCGATGCAGAGCCATATGTAAAACCCATAATAGACTTCCTAGTGAGAAATGAGGCGCCACTTCTTGCCAA |
|  | TGTGTACCCTTACTTTGCTTATGCGAATGATCAACAAAACAGTATTCCTCTTGCCTATGCTCTTTATACCCAACAAGGAAACAACG |
|  | ACGCTGGGTACCAAAACCTCTTCGATGCTATGTTGGATTCAATATACGCTGCAGTGGAGAAAGTGGGAGCATCCCAATTTGCAGAT |
|  | AGTGGTTTCTGAAAGAGATGGCCGAATTCCG |
| 7 | CGGGATCCGAGTTTGTTATGGAAGAAGTGCTGATGACCTCCCTACACCTGACAAGGTGGCACAGTTGGTTCAACTTCATAAAATC |
|  | AAATATGTCAGGATTTATGATTCTAATATACAGGTTCTGAAGGCCTTTGCAAACACTGGAATTGAGCTTATGATTGGGGTTCCAA |
|  | ATTCGGACTTGCTTTCATTCTCTCAGTTCCAATCTAATGCAGACTCTTGGCTGAAAAACAGCGTGCTTCCTTACTATCCGGCTAC |
|  | AAAGATCGCATACATCACTGTCGGCGCCGAAGTCACTGAGAGTCCTAACAATGCATCTTCATTTGTAGTGCCTGCCATGACCAAT |
|  | GTGCTTACAGCACTCAAGAAACTTGGGCTGCACAAAAAGATTAAAGTTTCCAGCACCCATTCCCTTGGGGTTTTGTCGCGATCCT |
|  | TCCCGCCTTCTGCTGGGGCTTTCAATAGCAGCCATGCACATTTCCTGAAGCCAATGCTAGAATTTCTTGCTGAAAATCAGTCACC |
|  | TTTTATGATTGATATATATCCTTATTATGCCCACCGTGATTCCCGGAGTAAAGTGTCTTTAGACTATGCCCGTTTGATGCATCC |
|  | TCTGAAGTAATTGATCCAAACACAGGCTTGCTGTACACAAACATGTTTGATGCCCAGATTGATGCTATTTACTTTGCACTGATGG |
|  | CCTTGGACTTCAGAACAATTAAGGTCATGGTCACTGAGTGCGGATGGCCGAATTCCG |
| 8 | CGGGATCCGGGGTGTGTTACGGCATGATGGGCGACAATCTACCACCGGCAAATGAAGTTGTAAGTCTTTACAAATCCAACGACATAA |
|  | TGAGAATGAGAATCTATAATCCTGATCAAGCTGCTTTACAAGCACTGGAATTTCGGGCATTGAGCTTATTCTTGGGGTGCTCCACC |
|  | AAGACCTTCAAGGCCTTGCCACCAATGCTAGCACTGCTCAACAATGGGTGCAAAGTAACGTGTTGAACTTTTGGCCTAGTGTCAAAA |
|  | TCAAGCACGTGGTAGTTGGCAACGAAATCAATCCTGTGGGAAGCTCTTCTGAGTTTGCCCAATATGTTCTACCTGCAATCCAAAACA |
|  | TATACCAAGCTATAAGAGCTCAAGGCCTTCAAGATCTAATCAAGGTTACAACAGCTATTGACATGACCCTGTTAGGAAACTCCTACC |
|  | CCCCATCACAAAGCTACTTCAGGACTGATGTGAGATCATACTTAGACCCCATAATTGGGTACTTGGTATATGCAAATGCACCTTTAC |
|  | TAGCCAATGTGTTGCCTTATTTTAGTTACTCCGATAACCCGATTGACATATCACTTTCCTATGCTCTTTTTAACTCAACAAATGTTG |
|  | TGGTTTGGGATGGTCAATATGGGTACCAAAATTTGTTTGATGCTATGTTGGATGCGGTGCATGTTGCAATTGATAACACAGGGATTG |
|  | GTTATGTGGAGGTTGTTGTATCCGAATGGGGTTGGCCGAATTCCG |
| 9 | CGGGATCCGGGGTTTGTTACGGAGGAAAAGGAAACAACCTACCAAAAATGCAAGCAGTGGTGGATTTATACAAATCAAACCGAATTG |
|  | ACAAAATCCGTTTATACCATCCAGACGAAGGAGCCCTTCAAGCCCTCAGAGGTTCAAACATAGAGGTGGTCCTCGGTGTCCCTAATG |
|  | ACCAACTTCAATCTCTCATCAATGTTGCAAATGCCACAAATTGGGTCAACAAGTACGTGAAAGCATACTCACAAAACGTGAAATTCA |

| SEQ ID NO | SEQUENCE |
|---|---|
| | AGTACATTGCAGTCGGTAACGAATTCTTTAGCAGGGTCTGTACTTCCAGCACTTGAAAACATTCAGAACGCAACTTCTGCCGCCAAT |
| | TTACAAGGCCAAATGAAGGTGTCAACAGCAATAGACACCACTTTACTTGGCAACTCTTACCCACCAAAAGATGGCGTTTTCAGCAGT |
| | AGTGCAAGTTCATACATAAGACCAATTGTAAACTTTTGAGCTAGAAATGGAGCTCCACTTCTCGCAAACGTGTACCCTTACTTCGCC |
| | TATGTTAACGACCAACAAAGCATTAGTCTCGACTATGCCTTGTTTACTGAACATGGTAACAACGAGGCTGGGTACCAAAACCTGTTT |
| | GATGCATTGTTGGATTCTCTATACGCTGCTCTTGAGAAAGTAGGGGCACCCAATGTGACGGTTGTTGTGTCTGAAACGGGCTGGCCG |
| 10 | CGGGATCCGGTGTTTGTTATGGAGTGATTGGTGATAATCTACCATCAAGGCAAGAAGTTGTGGACTTATATAAAACAAATGGCATTG |
| | GTAGAATGCGTATATACTACCCAGATGAAGAAGCACTCCAAGCCCTTAGAGGTTCAGGCATTGAGTTGATTATGGACGTGGCTAAG |
| | GAAACCCTTCAATCATTGACAGACTCCAATGCTGCTACAGATTGGGTCAATAAATATGTTACACCTTACTCGCAAGACGTCAATTT |
| | CAAGTACATCGCTGTTGGAAATGAAATTCATCCCAATACCAATGAGGCACAATATATTCTATCTGCCATGACCAACATTCAGAATG |
| | CAATTTCATCAGCAAATTTACAAATTAAGGTGTCAACAGCTATAGACTCTACTTTGATTACTAACTCTTACCCTCCCAATGATGGC |
| | GTTTTCACTAGCGATGCGGAGCCATACATAAAACCCATAATCAACTTCCTAGTGAGCAATGGGGCCCCAATTCTTGCCAACGTGTA |
| | CCCTTACTTTGCTTATGCAAATGATCAAAGCATTCCTCTTGCCTATGCTCTTTTTACCCAACAAGGAAACAACGACGTTGGGTACC |
| | AAAACCTCTTTGATGCTATGTTGGATTCAATATATGCTGCTTTGGAGAAAGTGGGAGCGTCCAATTTGCAGATAGTGGTTTCTGAG |
| | TGAGGATGGCCGAATTCCG |
| 11 | CGGGATCCGGTGTGTGTTACGGAGGAAATGGAAACAATCTACCAACAAAGCAAGCAGTGGTGGATCTTTACAAATCAAACAGAATA |
| | GGCAAAATCCGTTTATACTATCCAGACGAAGGAGTCCTTCAAGCCCTCAGAGGTTCAAACATAGAGGTGATCCTCGGTGTCCCTAA |
| | TGACCAACTTCATTCTCTCACCAACGCTGGAGCTGCCACAAATTGGGTCAACAAGTACGTGAAAGCATACTCACAAAACGTGAAAT |
| | TCAAGTACATTGCAGTTGGTAACGAAATTCACCCTGGTGACTCTTTAGCAGGGTCTGTACTTCCAGCACTTGAAAACATTCAGAAA |
| | GCAATTTCTGCCGCCAATTTACAAGGCCAAATGAAGGTGTCAACAGCAATAGACACCACTTTACTTGGCAACTCTTACCCACCAAA |
| | AGATGGCGTTTTCAGCAGTAGTGCAAGTTCATACATAAGACCAATTGTAAACTTTTTAGCAAGAAATGGAGCCCCACTTCTCGCAA |
| | ACGTGTACCCTTACTTCGCCTATGTTAACAACCAACAAAGCATTGGTCTTGACTATGCCTTGTTTACTAAACATGGTAACAACGAG |
| | GTTGGGTACCAAAACCTGTTTGATGCATTGCTGGATTCCCTATACGCTGCTCTTGAGAAAGTAGGGGCACCAAATGTGAAGGTTGT |
| | TGTGTCTGAGTGCGGATGGCCGAATTCCG |
| 12 | CGGAATTCGGCCATCCACTTTCGGATACAACAACCTCCACATAACCAATCTTAGTGTTATCAATGGCTGCATGTACTGAATCCAACA |
| | TAGCATCAAACAAATTTTGGTACCCATATTGACCATCCCATACCACAACATTTGGTGCTGTGAAAAGAGCATAGGGAAGTGATATGT |
| | CACGGGGGTTACCAGTGTAACTAAAATAAGGGTACACATTGACTAGTAATGGTGCATTTGCATATACCAAGTACCCAATTATGGGAT |
| | CTATGTATGATCTCACATCACCCCTGAAGGAACCTTGCGATGGAGGGAAAGATTTCCTATTAGGGTCATGTCAATATATGTTGAAAC |
| | CTTGATTTGATCNTGAAGGCCTTGAGCTCTTATTGCTTGGTATACATTTTGGATGGCAGGTAGAACATATTGGGCTACCGAAGAAGA |
| | GCCTCCAACGGGACTCACTTCATTTCCAACTGCCACGTACTTGATTTTGACACTAGGCCAGAAGTTCTACACGTTTTTTTGCACCCA |
| | TTGACGAGAAGTGTCAGGATTGGTGGCAAGGCCTTGAAGGTCAGAGTTTGGCACCCCAAGAATGAGTTCAATGCCAGAATTTCTAAG |
| | TGCTTCTAGAGCAGCTTGATTAGGATCATAGAGTCTCATTCTCTTTATGTTATTTGATCTATAAAGACCTATAACATCGTTTGCTGA |
| | CGGTAGATTGTTGCCCAGCATGCCGTA |

Vectors which comprise the above sequences are within the scope of the present invention, as are plants transformed with the above sequences. Vectors may be obtained from various commercial sources, including Clontech Laboratories, Inc. (Palo Alto, Calif.), Stratagene (La Jolla, Calif.), Invitrogen (Carlsbad, Calif.), New England Biolabs (Beverly, Me.) and Promega (Madison, Wis.).

Preferred vectors are those which are capable of transferring the sequences disclosed herein into plant cells or plant parts.

Methods to inhibit plant diseases, including use of a compound herein disclosed, according to the procedures described in U.S. Pat. No. 5,477,001, which patent is expressly incorporated by reference, are also part of the present invention.

Moreover, the most commercially significant use of the present invention is in the construction of "knockout mutants" using the above sequences, or known soybean sequences, for design and construction of male-sterile mutants. In other words, the present invention is informative to those skilled in the art as to their usefulness in making the naturally-occuring gene inactive. For example, the above sequences can be mutated by any means, i.e., deletion, insertion, point mutation, rearrangement, etc, so long as the mutated version retains the ability to recombine. The mutated version of the gene is then introduced into cells of a preferred soybean line via routine methods (ie. biolistic processes, lambda phage transformation, etc.). Male-sterile mutants of the preferred line would then be selected and propagated. These "knockout" mutant embryos, seeds and plants are within the scope of the present invention, as are the knockout constructs, ie. sequences and vectors.

In particular, sequences near the active sit of enzyme function, and the sit itself, would be preferred targets. For example, the codons for amino acid residues 240 through 250 would be a preferred knockout, but most preferred would be a construct wherein the codons encoding 245 through 248 were deleted.

For example, the following seeds, embryos or plants transformed with knockout constructs are considered within the present invention: soybean, maize, beet, tobacco, wheat, barley, poppy, rape, sunflower, alfalfa, sorghum, rose, carnation, gerbera, carrot, tomato, lettuce, chicory, pepper, melon and cabbage. Particularly preferred are: soybean, tobacco and maize. However, any seed, embryo or plant which gives rise to a plant which has a callose encasement of the microspores is within the scope of the present invention. Of course, those in the art recognize that any seed, embryo or plant transformed with knockout constructs which are useful for producing plants for biomass are within the scope of the present invention.

Transformation of cells with the compounds of the present invention can be accomplished according to known procedures. For example, infective, vector-containing bacterial strains (such as *Agrobacterium rhizogenes* and *Agrobacterium tumefaciens*) may be used for transformation. Zambryski, 43 *Ann. Rev. Pl. Physiol. Pl. Mol. Biol* 465 (1992). The following procedures are also well-known: Pollen-tube transformation [Zhon-xun et al., 6 *Plant Molec. Bio.* 165(1988)]; direct transformation of germinating seeds [Troepfer et al., 1 *Plant Cell* 133 (1989)]; polyethylene glycol or electroporation tranformation [Christou et al., 84 *Proc. Nat. Acad. Sci.* 3662 (1987)]; and biolistic processes [Yang & Cristou, *Particle Bombardment Technology for Gene Transfer* (1994)]. The transformed cells are also within the scope of the present invention.

The transformed cells may be induced to form transformed plants via organogenesis or embryogenesis, according to the procedures of Dixon *Plant Cell Culture: A Practical Approach* (IRL Press, Oxford 1987).

Therefore, also provided are methods for constructing sequences with the ability to knockout the above sequences, comprising one of the following techniques: inserting a foreign piece of DNA into one of the disclosed sequences; deleting a piece of DNA from one of the disclosed sequences; or creating a mutation such that the β-1,3-glucanase activity is eliminated.

Also provided are antisense constructs and methods to inhibit mRNA transcripts of the disclosed sequences, so as to either eliminate or reduce the amount of gene product. The procedures for antisense inhibition for mRNA are described in U.S. Pat. No. 5,554,743, which patent is expressly incorporated by reference into this application.

Also provided in the present invention are methods to improve seed germination, comprising expressing or over-expressing the β-1,3-glucanase(s) described herein, and using the glucanases to digest the callose wall of mature seeds [i.e., *Cucumis* Speices; Yim and Bradford, 114(3) Plant Physiology 289, abstract 1506 (1997)]. The seeds can then be germinated according to traditional methods. Overexpression can be as skill of the art, in particular, according to the procedures described in U.S. Pat. No. 5,477,001.

Lastly, the present invention includes methods to alter the naturally-occurring expression pattern of the β-1,3-glucanase genes so as to either delay or prematurely digest the callose wall. In other words, in a none-male-sterile plant, a glucanase gene is expressed (and the callose encasement digested) at a critical point in microsporogenesis called "the late tetrad stage." If the genes which digest the callose encasement are not active at the late tetrad stage, or if they are active before the late tetrad stage, the potential for pollen formation is lost. In the instance where the β-1,3-glucanase genes are expressed earlier than the late tetrad stage, the microspores would be too immature. In the case where the β-1,3-glucanase genes are expressed later than the late tetrad stage, the microspores would be arrested in development.

Since disease resistance is one characteristic conferred to a plant by the expression of β-1,3-glucanase, an ideal method would be to activate the sequences disclosed herein (or other glucanase sequences), and have the gene constitutively expressed thereafter. However, another embodiment of this invention is to alter the expression pattern so that the β-1,3-glucanase genes turn on later than the late tetrad stage. Constitutive expression thereafter may also be engineered. A preferred method in this regard is alteration of the regulatory regions of SEQ ID NO 7 so as to affect the expression of a β-1,3-glucanase either earlier or later than the late tetrad stage.

In particular, in order to practice the altered expression pattern aspect of the present invention, one would have to construct a vector which provided for either an early or late promoter in conjunction with the present sequences. For instance, the following promoters would be useful in early expression of the present sequences:

Ogs4B (Tsuchiya et al., 36 *Plant Cell Physiology* 487 (1994)

TA29 (Koltunow et al., 2 *Plant Cell* 1201 (1990)

A3 & A9 (Paul et al., 19 *Plant Molecular Biology* 611 (1992)

In order to then constitutively express the sequences described above, the construct optionally contains, for example, a 35S promoter.

Therefore, the present invention provides methods to express the β-1,3-glucanase genes described herein in a plant which has a callose encasement of microspores, at a time other than the late tetrad stage, comprising growing a plant transformed with a vector which allows expression at a time other than the late tetrad stage of a sequence selected from the group consisting of: SEQ ID NO 1; SEQ ID NO 2; SEQ ID NO 3; SEQ ID NO 4; SEQ ID NO 5; SEQ ID NO 6; SEQ ID NO 7; SEQ ID NO 8; SEQ ID NO 9; SEQ ID NO 10; SEQ ID NO 11 and SEQ ID NO 12.

A method as above, wherein the β-1,3-glucanase genes are then consititutively expressed is preferred.

Transformation of plants with these sequences would be according to known procedures as described above. Plants can be grown according to known procedures.

In addition, there are provided male-sterile soybean seeds, embryos and plants comprising a knockout construct of soybean β-1,3-glucanase gene, in particular, soybean seeds, embryos and plants wherein the soybean β-1,3-glucanase gene knocked out is SEQ ID NO 7 are provided.

EXAMPLES

EXAMPLE 1

NUCLEIC ACID MANIPULATIONS

Plant tissues for nucleic acid isolation were collected from the soybean cultivar Minsoy (PI 27890) grown in the greenhouse or growth chamber. Material for RNA extraction was immediately frozen in liquid nitrogen and stored at −80° C. until used. Soybean genomic DNA was extracted from freeze-dried young leaves, following the protocol by Keim et al., 15 *Soybean Genet. Newsl.* 150 (1988). Total DNA (10 μg) was digested and subjected to Southern blotting as described by Sambrook et al., *Molecular Cloning: A Laboratory Manual* (Cold Spring Harbor 1989). Total RNA was extracted using guanidinum isothiocyanate extraction according to Chamczynski & Sacchi, 162 *Anal. Biochem.* 156 (1987), electrophoresed on formaldehyde-agarose gels, and blotted onto Zeta Probe Nylon membrane (Biorad) as described by Sambrook et al. (above). Filters were prehybridized 3 house at 65° C. in 5× SSC, 2% SDS, 5× Denhardt's solution, 0.1 mg/ml herring sperm DNA. Hybridization was carried out overnight at 65° C. with 2× SSC+0.4% SDS and 1× SSC+0.4% SDS at 60° C. before exposure for autoradiography.

EXAMPLE 2

PCR AMPLIFICATION, CLONING AND SEQUENCE ANALYSIS

Coding region segments encoding β-1,3-glucanase were amplified from soybean genomic DNA and flower bud cDNA using primers that matched conserved sequences within the β-1,3-glucanases of other species as described by Simmons, 13 *Critical Rev. Plant Sci.* 325 (1994). To obtain cDNA, mRNA was prepared from flower buds, the mRNA was incubated with 5 μM random hexamers, 1 mM each of dATP, dCTP, dGTP and dTTP and 2 U/μl RNase inhibitor (Promega) in 10 mM Tris-HCl (pH 8.3), 50 M KCl, 2.5 M MgCl$^2$ for 30 min at 37° C., and then for a further 45 minutes at 37° C. following the addition of 20 U/μl superscript reverse transcriptase (BRL). After heating at 65° C. for 3 minutes, cDNA prepared from 0.1 μg of mRNA was used in the PCR experiments. Each 25 μl PCR contained 60 ng of soybean genomic DNA or 20 ng of flower cDNA, 10 mM Tris-HCl (pH 8.3), 50 mM KCl, 3 mM MgCl$^2$, 200 μM (each dATP, dCTP, dGTP, and dTTP, 2.5 U of Taq polymerase (BRL Life Technology), and 2 μM (each) PCR primer. PCR amplifications were performed according to the follwing schedule: 96° C. for 1 minute, 44° C. for 1 minute, 72° C. for 1 minute for 4 cycles, followed by 94° C. for 1 minute, 55° C. for 1 minute, 72° C. for 1 minute for 30 cycles. The 5' primer was 5'-CGCGGNGTNTGYTAYGG-3'; the 3' primer was 5'-CGCGGCCANCCNSWYTC-3' (where N=A, C,G,T; R=A,G; Y=C,T; S=C,G and W=A,T). The regions used correspond to amino acids 37–41 and 276–282 according to Simmons (see above). An aliquot of each PCR product was analyzed by agarose gel electrophoresis. A 700 bp fragment was cut from the gel and subjected to another round of PCR using identical conditions. Aliquots of these PCR products were digested with restriction enzymes recognixing 4 bp sites and the digestion products were compared with undigested DNA on agarose gels. The PCR products were cloned into the pGEM-T vector (Promega) and about 280 clones were tested by dot blot analysis (Sambrook et al, see above) to determine if they cross-hybridized with one another.

Cones were sequenced using Applied Biosystems Model 337 PRISM automated sequencer. DNA sequence analysis was carried out with the DNAsis (Hitachi), GCG (University of Wisconsin Genetics Computer Group, Madison) sequence analysis packages. Alignment of sequences was done using CLUSTAL W according to Thompson et al., 22 *Nucl. Acids Res.* 4673 (1994).

EXAMPLE 3

EXPRESSION PATTERNS OF GLUCANASES

In order to study gene-specific glucanase expression patters, the presence of mRNAs corresponding to each sequence disclosed herein was analyzed by RNA blot analyses using the gene-specific probes. The expression levels of all classes were quite low in young leaves. SEQ ID NOs 2, 4, 7 and 12 were highly expressed in young roots and hypocotyls. SEQ ID NO 7 was also expressed in the pod and flower bud. The mRNA transcripts of all β-1,3-glucanase genes were shown to be about 1.2 kb. mRNA from SEQ ID Nos 1, 3, 8 and 9 was undetectable, suggesting that these genes are either unexpressed, expressed at low level, or inducible.

Although the present invention has been fully described herein, it is to be noted that various changes and modifications are apparent to those skilled in the art. Such changes and modifications are to be understood as included within the scope of the present invention as defined by the appended claims.

What is claimed is:

1. An isolated DNA molecule selected from the group consisting of: SEQ ID NO 1; SEQ ID NO 2; SEQ ID NO 3; SEQ ID NO 4; SEQ ID NO 5; SEQ ID NO 6; SEQ ID NO 7; SEQ ID NO 8; SEQ ID NO 9; SEQ ID NO 10; SEQ ID NO 11 and SEQ ID NO 12.

2. A knockout construct of SEQ ID NO 7.

3. A vector comprising a knockout construct of SEQ ID NO 7.

4. A seed comprising a knockout construct of SEQ ID NO 7.

5. An embryo comprising a knockout construct of SEQ ID NO 7.

6. A plant comprising a knockout construct of SEQ ID NO 7.

7. A method to construct a male-sterile knockout mutant, comprising: transforming a plurality of plant cells with a knockout construct of SEQ ID NO 7; and inducing the plurality of plant cells to grow into a plant; and selecting those plants which are male-sterile.

8. A plant embryo comprising a vector which allows expression at a time other than the late tetrad stage of SEQ ID NO 7.

9. A plant seed comprising a vector which allows expression at a time other than the late tetrad stage of SEQ ID NO 7.

10. A plant comprising a vector which allows expression at a time other than the late tetrad stage of SEQ ID NO 7.

11. A method to express β-1,3-glucanase in a plant which has a callose encasement of microspores, at a time other than the late tetrad stage, comprising growing a plant transformed with a vector which allows expression at a time other than the late tetrad stage of SEQ ID NO 7.

12. A method to degrade the callose of seeds, comprising expressing SEQ ID NO 7 so as to produce an expression product, and allowing the expression product adequate time and conditions to degrade said callose.

13. A male-sterile soybean seed comprising a knockout construct of SEQ ID NO 7.

* * * * *

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 741 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:1:

CGGGATCCGG GGTGTGTTAC GGCATGATGG GCGACAATCT ACCACCGGCA AATGAAGTTG        60

TAAGTCTTTA CAAATCCAAC GACATAATGA GAATGAGAAT CTATAATCCT GATCAAGCTG       120

CTTTACAAGC ACTGGGAAAT TCGGGCATTG AGCTTATTCT TGGGGTGCTC CACCAAGACC       180

TTCAAGGCCT TGCCACCAAT GCTAGCACTG CTCAACAATG GGTGCAAAGT AACGTGTTGA       240

ACTTTTGGCC TAGTGTCAAA ATCAAGCACG TGGTAGTTGG CAACGAAATC AATCCTGTGG       300

GAAGCTCTTC TGAGTTTGCC CAATATGTTC TACCTGCAAT CCAAAACATA TACCAAGCTA       360

TAAGAGCTCA AGGCCTTCAA GATCTAATCA AGGTTACAAC AGCTATTGAC ATGACCCTGT       420

TAGGAAACTC CTACCCCCCA TCACAAAGCT ACTTCAGGAC TGATGTGAGA TCATACTTAG       480

ACCCCATAAT TGGGTACTTG GTATATGCAA ATGCACCTTT ACTAGCCAAT GTGTTGCCTT       540

ATTTTAGTTA CTCCAATAAC CCGATTGACA TATCACTTTC CTATGCTCTT TTTAACTCAA       600

CAAATGTTGT GGTTTGGGAT GGTCAATATG GGTACCAAAA TTTGTTTGAT GCTATGTTGG       660

ATGCGGTGCA TGTTGCAATT GATAACACAG GGATTGGTTA TGTGGAGGTT GTTGTATCCG       720

AGAGAGGTTG GCCGAATTCC G                                                741

(2) INFORMATION FOR SEQ ID NO:2:

(i) SEQUENCE CHARACTERISTICS:
            (A) LENGTH: 735 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:2:

CGGGATCCGG CGTGTGTTAT GGAAGACTTG GCAACAACTT ACCAACCCCT CAAGAAGTTG        60

TGGCCCTCTA CAATCAAGCC AACATTCGCA GGATGCGAAT CTACGGTCCA AGCCCAGAAG       120

TCCTCGAAGC ACTAAGAGGT TCCAACATTG AGCTTTTGCT AGACATTCCA AATGACAACC       180

TCAGAAACCT AGCATCTAGC CAAGACAATG CAAACAAATG GGTGCAAGAC AACATCAAAA       240

ACTATGCCAA CAATGTCAGA TTCAGATACG TTTCAGTGGG AAATGAAGTG AAACCCGAAC       300

ACTCATTTGC ACAATTTCTA GTGCCTGCAT TGGAAAACAT TCAGAGGGCC ATTTCTAATG       360

CTGGCCTTGG AAACCAAGTA AAAGTTTCCA CTGCCATTGA TACTGGTGCC TTGGCAGAAT       420

CATTCCCACC ATCAAAGGGT TCCTTCAAAT CTGATTATAG AGGAGCATAT CTTGATGGTG       480

TCATCAGATT TCTAGTGAAC AATAATGCCC CATTAATGGT TAATGTGTAC TCTTACTTCG       540

CTTACACTGC AAACCCTAAG GACATTAGTC TTGACTATGC ACTTTTTAGG TCTCCTTCGG       600

TGGTAGTGCA AGATGGTTCA CTTGGTTACC GTAACCTCTT TGATGCTTCG GTTGATGCTG       660

TTTATGCTGC ATTGGAGAAA GCAGGAGGAG GGTCATTGAA CATAGTTGTG TCTGAGTGAG       720

GATGGCCGAA TTCCG                                                       735

(2) INFORMATION FOR SEQ ID NO:3:

(i) SEQUENCE CHARACTERISTICS:
            (A) LENGTH: 717 base pairs (B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:3:

```
CGGGATCCGG AGTTTGCTAT GGAGTACTCG GTAATAATCT ACCATCAAGG CAAGAAGTTG      60
TGGACTTGTA TAAAACAAAT GGGATAGGTA GAATGCGTAT ATACTATCCA GATGAAGAAG     120
CGCTCCAAGC CCTTAGAGGT TCAGGCATTG AGTTGATTAT GGACGTGGCT AAGGAAACCC     180
TTCAATCAAT GACAGACCCC AATGCTGCTA CAGATTGGGT CAATAAGTAT GTTACAGCCT     240
ACTCGCAAGA CGTCAATTTC AAGTACATCG CTGTTGGAAA TGAAATTCAC CCCAATACCA     300
ATGAGGCACA GTACATTCTA TCTGCCATGA CCAACATTCA GAATGCAATT TCATCAGCCA     360
ATTTACAAAT CAAGGTGTCA ACAGCAATAG ACTCTACTTT CATTGCTCCG CCCTCCTATC     420
CACCCAATGA TGCTGTTTTC ACTAGCGATG CAGAGCCATA TGTAAAACCC ATAATAGACT     480
TCCTAGTGAG AAATGAGGCG CCACTTCTTG CCAATGTGTA CCCTTACTTT GCTTATGCGA     540
ATGATCAACA AAACAGTATT CCTCTTGCCT ATGCTCTTTT TACCCAACAA GGAAACAACG     600
ACGCTGGGTA CCAAAACCTC TTCGATGCTA TGTTGGATTC AATATACGCT GCAGTGGAGA     660
AAGTGGGAGC ATCCAATTTG CAGATAGTGG TTTCTGAATC TGGTTGGCCG AATTCCG        717
```

(2) INFORMATION FOR SEQ ID NO:4:

(i) SEQUENCE CHARACTERISTICS:
(A) LENGTH: 745 base pairs
(B) TYPE: nucleic acid
(C) STRANDEDNESS: single
(D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:4:

```
CCTAAACTAC GTGCGGGATC CGGGGTATGT TATGGCATGC TGGGCAACAA TCTACCATCA      60
GCAAACGAAG TTATAGGTCT TTATAGATCA AATAACATAA GGAGAATGAG ACTCTATGAT     120
CCTAATCAAG CTGCTCTAGA AGCACTTAGA AATTCTGGCA TTGAACTCAT TCTTGGGGTG     180
CCAAACTCTG ACCTTCAAGG CCTTGCCACC AATCCTGACA CTTCTCGTCA ATGGGTGCAA     240
AAAAACGTGT TGAACTTTTG GCCTAGTGTC AAAATCAAGT ACGTGGCAGT TGGAAATGAA     300
CTGAGTCCCG TTGGACGCTC TTCTTCGGTA GCCCAATATG TTCTACCTGC CATCCAAAAT     360
GTATACCAAG CAATAAGAGC TCAAGGCCTT CATGATCAAA TCAAGGTTTC AACATCTATT     420
GACATGACCC TAATAGGAAA CTCTTTCCCT CCACCGCAAG GTTCCTTCAG GGGTGATGTG     480
TGATCATACC TAGATCCCAT AATTGGGTAC TTGGTATATG CAAATGCACC ATTACTAGTC     540
AATGTGTACC CTTATTTTAG TTACACTGGT AACCCCGTG ACATATCACT TCCCTATGCT      600
CTTTTCACAG CACCAAATGT TGTGGTATGG GATGGTCAAT ATGGGTACCA AAATTTGTTT     660
GATGCTATGT TGGATTCAGT ACATGCAGCC ATTGATAACA CTAAGATTGG TTATGTGGAG     720
GTTGTTGTAT CCGAAAGCGG ATGGA                                          745
```

(2) INFORMATION FOR SEQ ID NO:5:

(i) SEQUENCE CHARACTERISTICS:
        (A) LENGTH: 718 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:5:

```
CGGGCATCCG GTGTCTGTTA CGGAGGAAAT GGAAACAATC TACCAACAAA GCAAGCAGTG    60
GTGGATCTTT ACAAATCAAA CAGAATAGGC AAAATCCGTT TATACTATCC AGACGAAGGA   120
GTCCTTCAAG CCCTCAGAGG TTCAAACATA GAGGTGATCC TCGGTGTCCC TAATGACCAA   180
CTTCAATCTC TCACCAACGC TGGAGCTGCC ACAAATTGGG TCAACAAGTA CGTGAAAGCA   240
TACTCACAAA ACGTGAAATT CAAGTACATT GCAGTTGGTA ACGAAATTCA CCCTGGTGAC   300
TCTTTAGCAG GGTCTGTACT TCCAGCACTT GAAACCATTG AGAAAGCAAT TTCTGCCGCC   360
AATTTACAAG GCCAAATGAA GGTGTCAACA GCAATAGACA CCACTTTACT TGGCAACTCT   420
TACCCACCAA AAGATGGCGT TTTCAGCAGT AGTGCAAGTT CATACATAAG ACCAATTGTA   480
AACTTTTTAG CAAGAAATGG AGCCCCACTT CTCGCAAACG TGTACCCTTA CTTCGCCTAT   540
GTTAACAACC AACAAAGCAC TGGTCTTGAC TATGCCTTGT TTACTAAACA TGGTAACAAC   600
GAGGTTGGGT ACCAAAACCT GTTTGATGCA TTGTTGGATT CTCTATACGC TGCTCTTGAG   660
AAAGTAGGGG CACCAAATGT GAAGGTTGTT GTGTCTGAAA GAGGTTGGCC GAATTCCG     718
```

(2) INFORMATION FOR SEQ ID NO:6:

(i) SEQUENCE CHARACTERISTICS:
        (A) LENGTH: 719 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:6:

```
CGGGATCCGG GAGTATGTTA CGGGAGTACT CGGTAATAAT CTACCATCAA GGCAAGAAGT    60
TGTGGACTTG TATAAAACAA ATGGGATAGG TAGAATGCGT ATATACTATC CAGATGAAGA   120
AGCACTCCAA GCCCTTAGAG GTTCAGGCAT TGAGTTGATT ATGGACGTGG CTAAGGAAAC   180
CCTTCAGTCA ATGACAGACC CCAATGCTGC TACAGATTGG GTCAATAAGT ATGTTACAGC   240
CTACTCGCAA GACGTCAATT TCAAGTACAT CGCTGTTGGA AATGAAATTC ACCCCAATAC   300
CAATGAGGCA CAGTACATTC TATCTGCCAT GACCAACATT CAGAATGCAA TTTCATCAGC   360
CAATTTACAA ATCAAGGTGT CAACAGCAAT AGACTCTACT TTCATTGCTC CGCCCTCCTA   420
TCCACCCAAT GATGCTGTTT TCACTAGCGA TGCAGAGCCA TATGTAAAAC CCATAATAGA   480
CTTCCTAGTG AGAAATGAGG CGCCACTTCT TGCCAATGTG TACCCTTACT TGCTTATGC    540
GAATGATCAA CAAAACAGTA TTCCTCTTGC CTATGCTCTT TATACCCAAC AAGGAAACAA   600
CGACGCTGGG TACCAAAACC TCTTCGATGC TATGTTGGAT TCAATATACG CTGCAGTGGA   660
GAAAGTGGGA GCATCCCAAT TTGCAGATAG TGGTTTCTGA AAGAGATGGC CGAATTCCG    719
```

(2) INFORMATION FOR SEQ ID NO:7:

(i) SEQUENCE CHARACTERISTICS:
        (A) LENGTH: 737 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:7:

```
CGGGATCCGA GTTTGTTATG GAAGAAGTGC TGATGACCTC CCTACACCTG ACAAGGTGGC      60

ACAGTTGGTT CAACTTCATA AAATCAAATA TGTCAGGATT TATGATTCTA ATATACAGGT     120

TCTGAAGGCC TTTGCAAACA CTGGAATTGA GCTTATGATT GGGGTTCCAA ATTCGGACTT     180

GCTTTCATTC TCTCAGTTCC AATCTAATGC AGACTCTTGG CTGAAAAACA GCGTGCTTCC     240

TTACTATCCG GCTACAAAGA TCGCATACAT CACTGTCGGC GCCGAAGTCA CTGAGAGTCC     300

TAACAATGCA TCTTCATTTG TAGTGCCTGC CATGACCAAT GTGCTTACAG CACTCAAGAA     360

ACTTGGGCTG CACAAAAAGA TTAAAGTTTC CAGCACCCAT TCCCTTGGGG TTTTGTCGCG     420

ATCCTTCCCG CCTTCTGCTG GGCTTTCAA TAGCAGCCAT GCACATTTCC TGAAGCCAAT     480

GCTAGAATTT CTTGCTGAAA ATCAGTCACC TTTTATGATT GATATATATC CTTATTATGC     540

CCACCGTGAT TCCCGGAGTA AAGTGTCTTT AGACTATGCC CTGTTTGATG CATCCTCTGA     600

AGTAATTGAT CCAAACACAG GCTTGCTGTA CACAAACATG TTTGATGCCC AGATTGATGC     660

TATTTACTTT GCACTGATGG CCTTGGACTT CAGAACAATT AAGGTCATGG TCACTGAGTG     720

CGGATGGCCG AATTCCG                                                   737
```

(2) INFORMATION FOR SEQ ID NO:8:

(i) SEQUENCE CHARACTERISTICS:
        (A) LENGTH: 741 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:8:

```
CGGGATCCGG GGTGTGTTAC GGCATGATGG GCGACAATCT ACCACCGGCA AATGAAGTTG      60

TAAGTCTTTA CAAATCCAAC GACATAATGA GAATGAGAAT CTATAATCCT GATCAAGCTG     120

CTTTACAAGC ACTGGGAATT TCGGGCATTG AGCTTATTCT TGGGGTGCTC CACCAAGACC     180

TTCAAGGCCT TGCCACCAAT GCTAGCACTG CTCAACAATG GGTGCAAAGT AACGTGTTGA     240

ACTTTTGGCC TAGTGTCAAA ATCAAGCACG TGGTAGTTGG CAACGAAATC AATCCTGTGG     300

GAAGCTCTTC TGAGTTTGCC CAATATGTTC TACCTGCAAT CCAAAACATA TACCAAGCTA     360

TAAGAGCTCA AGGCCTTCAA GATCTAATCA AGGTTACAAC AGCTATTGAC ATGACCCTGT     420

TAGGAAACTC CTACCCCCCA TCACAAAGCT ACTTCAGGAC TGATGTGAGA TCATACTTAG     480

ACCCCATAAT TGGGTACTTG GTATATGCAA ATGCACCTTT ACTAGCCAAT GTGTTGCCTT     540

ATTTTAGTTA CTCCGATAAC CCGATTGACA TATCACTTTC CTATGCTCTT TTTAACTCAA     600
```

| | |
|---|---|
| CAAATGTTGT GGTTTGGGAT GGTCAATATG GGTACCAAAA TTTGTTTGAT GCTATGTTGG | 660 |
| ATGCGGTGCA TGTTGCAATT GATAACACAG GGATTGGTTA TGTGGAGGTT GTTGTATCCG | 720 |
| AATGGGGTTG GCCGAATTCC G | 741 |

(2) INFORMATION FOR SEQ ID NO:9:

(i) SEQUENCE CHARACTERISTICS:
  (A) LENGTH: 696 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:9:

| | |
|---|---|
| CGGGATCCGG GGTTTGTTAC GGAGGAAAAG GAAACAACCT ACCAAAAATG CAAGCAGTGG | 60 |
| TGGATTTATA CAAATCAAAC CGAATTGACA AAATCCGTTT ATACCATCCA GACGAAGGAG | 120 |
| CCCTTCAAGC CCTCAGAGGT TCAAACATAG AGGTGGTCCT CGGTGTCCCT AATGACCAAC | 180 |
| TTCAATCTCT CATCAATGTT GCAAATGCCA CAAATTGGGT CAACAAGTAC GTGAAAGCAT | 240 |
| ACTCACAAAA CGTGAAATTC AAGTACATTG CAGTCGGTAA CGAATTCTTT AGCAGGGTCT | 300 |
| GTACTTCCAG CACTTGAAAA CATTCAGAAC GCAACTTCTG CCGCCAATTT ACAAGGCCAA | 360 |
| ATGAAGGTGT CAACAGCAAT AGACACCACT TTACTTGGCA ACTCTTACCC ACCAAAAGAT | 420 |
| GGCGTTTTCA GCAGTAGTGC AAGTTCATAC ATAAGACCAA TTGTAAACTT TTGAGCTAGA | 480 |
| AATGGAGCTC CACTTCTCGC AAACGTGTAC CCTTACTTCG CCTATGTTAA CGACCAACAA | 540 |
| AGCATTAGTC TCGACTATGC CTTGTTTACT GAACATGGTA ACAACGAGGC TGGGTACCAA | 600 |
| AACCTGTTTG ATGCATTGTT GGATTCTCTA TACGCTGCTC TTGAGAAAGT AGGGGCACCC | 660 |
| AATGTGACGG TTGTTGTGTC TGAAACGGGC TGGCCG | 696 |

(2) INFORMATION FOR SEQ ID NO:10:

(i) SEQUENCE CHARACTERISTICS:
  (A) LENGTH: 708 base pairs
  (B) TYPE: nucleic acid
  (C) STRANDEDNESS: single
  (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:10:

| | |
|---|---|
| CGGGATCCGG TGTTTGTTAT GGAGTGATTG GTGATAATCT ACCATCAAGG CAAGAAGTTG | 60 |
| TGGACTTATA TAAAACAAAT GGCATTGGTA GAATGCGTAT ATACTACCCA GATGAAGAAG | 120 |
| CACTCCAAGC CCTTAGAGGT TCAGGCATTG AGTTGATTAT GGACGTGGCT AAGGAAACCC | 180 |
| TTCAATCATT GACAGACTCC AATGCTGCTA CAGATTGGGT CAATAAATAT GTTACACCTT | 240 |
| ACTCGCAAGA CGTCAATTTC AAGTACATCG CTGTTGGAAA TGAAATTCAT CCCAATACCA | 300 |
| ATGAGGCACA ATATATTCTA TCTGCCATGA CCAACATTCA GAATGCAATT TCATCAGCAA | 360 |
| ATTTACAAAT TAAGGTGTCA ACAGCTATAG ACTCTACTTT GATTACTAAC TCTTACCCTC | 420 |
| CCAATGATGG CGTTTTCACT AGCGATGCGG AGCCATACAT AAAACCCATA ATCAACTTCC | 480 |

TAGTGAGCAA TGGGGCCCCA ATTCTTGCCA ACGTGTACCC TTACTTTGCT TATGCAAATG    540

ATCAAAGCAT TCCTCTTGCC TATGCTCTTT TTACCCAACA AGGAAACAAC GACGTTGGGT    600

ACCAAAACCT CTTTGATGCT ATGTTGGATT CAATATATGC TGCTTTGGAG AAAGTGGGAG    660

CGTCCAATTT GCAGATAGTG GTTTCTGAGT GAGGATGGCC GAATTCCG    708

(2) INFORMATION FOR SEQ ID NO:11:

(i) SEQUENCE CHARACTERISTICS:
        (A) LENGTH: 717 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:11:

CGGGATCCGG TGTGTGTTAC GGAGGAAATG GAAACAATCT ACCAACAAAG CAAGCAGTGG     60

TGGATCTTTA CAAATCAAAC AGAATAGGCA AAATCCGTTT ATACTATCCA GACGAAGGAG    120

TCCTTCAAGC CCTCAGAGGT TCAAACATAG AGGTGATCCT CGGTGTCCCT AATGACCAAC    180

TTCATTCTCT CACCAACGCT GGAGCTGCCA CAAATTGGGT CAACAAGTAC GTGAAAGCAT    240

ACTCACAAAA CGTGAAATTC AAGTACATTG CAGTTGGTAA CGAAATTCAC CCTGGTGACT    300

CTTTAGCAGG GTCTGTACTT CCAGCACTTG AAAACATTCA GAAAGCAATT TCTGCCGCCA    360

ATTTACAAGG CCAAATGAAG GTGTCAACAG CAATAGACAC CACTTTACTT GGCAACTCTT    420

ACCCACCAAA AGATGGCGTT TTCAGCAGTA GTGCAAGTTC ATACATAAGA CCAATTGTAA    480

ACTTTTTAGC AAGAAATGGA GCCCCACTTC TCGCAAACGT GTACCCTTAC TTCGCCTATG    540

TTAACAACCA ACAAAGCATT GGTCTTGACT ATGCCTTGTT TACTAAACAT GGTAACAACG    600

AGGTTGGGTA CCAAAACCTG TTTGATGCAT TGCTGGATTC CCTATACGCT GCTCTTGAGA    660

AAGTAGGGGC ACCAAATGTG AAGGTTGTTG TGTCTGAGTG CGGATGGCCG AATTCCG      717

(2) INFORMATION FOR SEQ ID NO:12:

(i) SEQUENCE CHARACTERISTICS:
        (A) LENGTH: 722 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:12:

CGGAATTCGG CCATCCACTT TCGGATACAA CAACCTCCAC ATAACCAATC TTAGTGTTAT     60

CAATGGCTGC ATGTACTGAA TCCAACATAG CATCAAACAA ATTTTGGTAC CCATATTGAC    120

CATCCCATAC CACAACATTT GGTGCTGTGA AAAGAGCATA GGGAAGTGAT ATGTCACGGG    180

GGTTACCAGT GTAACTAAAA TAAGGGTACA CATTGACTAG TAATGGTGCA TTTGCATATA    240

CCAAGTACCC AATTATGGGA TCTATGTATG ATCTCACATC ACCCCTGAAG GAACCTTGCG    300

ATGGAGGGAA AGATTTCCTA TTAGGGTCAT GTCAATATAT GTTGAAACCT TGATTTGATC    360

TGAAGGCCTT GAGCTCTTAT TGCTTGGTAT ACATTTTGGA TGGCAGGTAG AACATATTGG    420

```
GCTACCGAAG AAGAGCCTCC AACGGGACTC ACTTCATTTC CAACTGCCAC GTACTTGATT    480

TTGACACTAG GCCAGAAGTT CTACACGTTT TTTTGCACCC ATTGACGAGA AGTGTCAGGA    540

TTGGTGGCAA GGCCTTGAAG GTCAGAGTTT GGCACCCCAA GAATGAGTTC AATGCCAGAA    600

TTTCTAAGTG CTTCTAGAGC AGCTTGATTA GGATCATAGA GTCTCATTCT CTTTATGTTA    660

TTTGATCTAT AAAGACCTAT AACATCGTTT GCTGACGGTA GATTGTTGCC CAGCATGCCG    720

TA                                                                  722
```